United States Patent
Moller (10) Patent No.: US 8,267,901 B2
(45) Date of Patent: Sep. 18, 2012

(54) DOSE DELIVERY DEVICE WITH GEARING MECHANISM

(76) Inventor: Claus Schmidt Moller, Fredensborg (DK)

(*) Notice: Subject to any disclaimer, the term of this patent is extended or adjusted under 35 U.S.C. 154(b) by 13 days.

(21) Appl. No.: 12/680,016

(22) PCT Filed: Sep. 25, 2008

(86) PCT No.: PCT/DK2008/000334
§ 371 (c)(1),
(2), (4) Date: Jun. 28, 2010

(87) PCT Pub. No.: WO2009/039851
PCT Pub. Date: Apr. 2, 2009

(65) Prior Publication Data
US 2010/0268171 A1    Oct. 21, 2010

(30) Foreign Application Priority Data

Sep. 25, 2007 (DK) .................................. 2007 01374
Apr. 19, 2008 (DK) .................................. 2008 00568

(51) Int. Cl.
*A61M 5/00* (2006.01)
(52) U.S. Cl. ........................................ 604/211; 604/246
(58) Field of Classification Search .................. 604/246, 604/207, 135, 208–211, 187
See application file for complete search history.

(56) References Cited

U.S. PATENT DOCUMENTS

2006/0184117 A1* 8/2006 Knight et al. ................. 604/135
2006/0206057 A1* 9/2006 DeRuntz et al. ............. 604/224

FOREIGN PATENT DOCUMENTS

| DE | 20317377 U1 | 4/2005 |
|----|-------------|--------|
| EP | 0327910 A2 | 8/1989 |
| EP | 1003581 B1 | 5/2000 |
| EP | 1568389 A1 | 8/2005 |
| WO | 9413344 A1 | 6/1994 |
| WO | 2005018721 A1 | 3/2005 |
| WO | 2006072188 A1 | 7/2006 |
| WO | 2006114396 A1 | 11/2006 |
| WO | 2007104697 A2 | 9/2007 |

OTHER PUBLICATIONS

International Search Report PCT/DK2008/000334; Dated Jan. 26, 2009.

* cited by examiner

*Primary Examiner* — Kevin C Sirmons
*Assistant Examiner* — Michael J Anderson
(74) *Attorney, Agent, or Firm* — Cantor Colburn LLP (57) ABSTRACT

A dose delivery device is disclosed where a dose can be set by rotating a dose setting member, whereby a push button is elevated from one end of the device a distance proportional to the set dose from a position fixed relative to the housing, and where the set dose can then be injected by pressing the push button back to its non-elevated position, through which motion a piston rod will move the same or a different distance due to a gearing mechanism being provided between the push button and the piston rod, where the gearing mechanism includes at least a first and a second thread on one or more parts that are rotationally coupled to each other, the first thread engaging a driver, the second thread engaging an element rotationally locked to the driver, one of the threads of the gearing mechanism being left-handed and the other one being right-handed.

4 Claims, 10 Drawing Sheets

DOSE DELIVERY DEVICE WITH GEARING MECHANISM

TECHNICAL FIELD

The invention relates to a dose delivery device, wherein a dose can be set by rotating a dose setting member, whereby a push button is elevated from one end of the device, and the set dose can then be injected by pressing the push button back to its non-elevated position, thereby moving a piston rod cooperating with the piston in a cartridge and expelling a medicament out of the cartridge through a needle.

BACKGROUND

From EP 0 327 910 is known an injection device in which a dose is set in the classic way by rotating a tubular injection button engaging a threaded piston rod, thereby causing the injection button to elevate from the end of the injection device. By pressing down the injection button until abutment with a fixed stop, the threaded piston rod is moved a distance corresponding to the movement of the injection button. The piston rod mates a piston in a cartridge and medicine is expelled from the cartridge. This kind of injection device transmits the injection force directly to the piston of the cartridge but provides no gearing, i.e. the linear movement of the injection button corresponds exactly to the linear movement of the piston rod.

As a little amount of a medicament by directly transmitted injection force, causes a very little movement of the injection button, it is an advantage with a gearing ratio between the injection button and the piston rod to make it more clear to the patient, whether the injection is foregoing or not. Users having reduced finger strength could at the same time want a reduced injection force needed to carry out an injection.

EP 1 003 581 describes a number of methods to achieve a dose setting providing a gearing between the axial movement of the piston rod and the dose setting member. In one embodiment a dose setting member is rotated in a thread in the housing having a higher pitch than the pitch on the piston rod. When pressure is added to an injection button, the piston rod is being rotationally coupled to the dose setting member and as the piston rod is rotated in a nut fixed to the housing it is moved forward until the dose setting member abuts a fixed stop. This embodiment provides a gearing in movement, but does not reduce the needed injection force very much, as the transmission from linear movement to rotational movement and back from rotational to linear movement eats up most of the obtained force reduction due to friction.

A dose setting device, wherein a gearing provides both a longer injection button movement when setting the dose and a following lower injection pressure is described in WO 94/13344. This dose setting mechanism comprises a flat rotatable dose setting element engaged with an injection button, a dose administration wheel connected with a piston rod and a coupling ring connected with the dose setting element and injection button. Only when pressing the injection button, the coupling ring will engage the dose administration wheel, and as the gearwheel connection between the dose setting element and the injection button has a larger diameter than the gearwheel connection between the administration wheel and the piston rod, a gearing with a little loss of force due to friction is obtained. However, this development provides a complicated voluminous mechanical solution which demands high precision.

EP 1 568 389 describes a pen with a gearing with a very little loss of injection force due to friction. A nut is rotated along a threaded piston rod. The nut is provided with a gearwheel on the side, which on one side engages the housing and on the other side elevates an injection button. When the injection button is pushed, the nut and the piston rod are moved with a gearing ratio of 2:1 between the injection button and the piston rod. As none of the parts of the injection mechanism rotate in threads during injection, the loss of force due to friction is very limited. However, this mechanism is rather complicated, and it is not suited for simple, disposable dose delivery devices.

WO 2005/018721 describes a pen with a gearing mechanism based on two threads handed in the same direction and a third thread on the piston rod which is not directly a part of the gearing mechanism. A piston rod is connected with a nut. A non-rotational driver is engaging a scale drum via a first thread and the nut via a second thread. The pitch of the first thread is bigger then the pitch of the second pitch and the difference between them is equal to the pitch of the piston rod. When a dose is set, the nut is rotationally locked to the scale drum, and is thereby rotated and elevated a distance corresponding to the elevation of the driver. When the set dose is to be injected, the nut disengages the scale drum to engage the non-rotational driver. As the scale drum is pushed into the device, the rotation of the scale drum will cause the non-rotational driver to retract into the scale drum and the resulting displacement of the driver to be equal to the set dose. The nut is now pushed back to zero position bringing the piston rod along causing insulin to be expelled. It should be noted however that the pitches of the threads are dependant of number of increments per revolution, unit size etc. and the dose force will be relatively high due to the low driving pitch.

In WO 2006/072188 a pen with a similar kind of gearing is described. A scale drum with an outer and an inner thread is engaging the housing via the outer thread and a non-rotational driver via the inner thread. When the scale drum is rotated to set a dose, the scale drum will elevate a certain distance per unit, and the driver will elevate another and smaller distance as it is both elevated directly by the scale drum and rotated back into the pen due to the thread engagement with the scale drum. The driver is engaging a piston rod via a linear one-way ratchet which allows relative movement between the piston rod and the driver when a dose is set, but will carry the piston rod along expelling insulin when the set dose is injected. Like in the previously mentioned concept, the pitches of the threads are dependant of number of increments per revolution, unit size etc. and the dose force will be relatively high due to the low driving pitch. Further more this concept does not allow the user to correct a wrongly set dose.

The disclosure seeks to provide a gearing mechanism comprising a few and simple parts, with a very low injection force and a relative short movement of the injection button during injection.

BRIEF SUMMARY

The disclosure relates to a dose delivery device comprising a housing, a dose setting member, a push button, a piston rod rotationally locked to the housing during dose setting and injection, a driver rotationally locked to the housing, and a gearing mechanism being provided between the push button and the piston rod, wherein a dose can be set by rotating the dose setting member, whereby the push button is elevated from one end of the device a distance proportional to the set dose from a position fixed relative to the housing, and wherein the set dose can then be injected by pressing the push button back to its non-elevated position, through which motion of the push button the piston rod will move the same or a different distance due to the gearing, the gearing mechanism comprising at least a first and a second thread on one or more parts that are rotationally coupled to each other, the first thread engaging the driver, the second thread engaging an element rotationally locked to the driver, characterised by one of the first and second threads of the gearing mechanism being left-handed and the other one being right-handed.

By using threads of opposite direction, very high pitches can be used and, thus, very small force reductions due to friction can be obtained.

In an embodiment of the invention, the dose setting member and the push button is formed as one integral part. Hereby it is achieved that the number of parts and, thus, the complexity and production costs of the device are reduced.

In yet an embodiment of the invention, the gearing mechanism comprises at least one dual-threaded nut, onto which the first and second threads are placed. By placing the first and second threads on a common nut, it is achieved that the number of parts and, thus the complexity and production costs of the device are reduced.

In a further embodiment of the invention, the dose delivery device further comprises a dosing nut being engaged to the piston rod via a thread and being rotationally coupled to the dose setting member. This makes the interface between the gearing mechanism and the piston safer than e.g. a linear one-way ratchet.

In an embodiment of the invention, the dose delivery device further comprises a cartridge holder, and the piston rod is set free to rotate when the cartridge holder is demounted. Hereby it is made possible to exchange the cartridge holder and, thus, reload the dose delivery device.

In another embodiment of the invention, the dose delivery device further comprises a cartridge holder, and the housing and the cartridge holder are moulded as one part. Hereby it is achieved that the number of parts and, thus the complexity and production costs of the device are reduced.

In an embodiment of the invention, the dose delivery device further comprises a scale drum not being spring loaded against any other part of the device. This makes it easier to make the scale drum rotate back to its zero position during injection In a further embodiment of the invention, the dose delivery device further comprises a dosing ratchet, and the dose setting member and the scale drum are rotationally connected to each other only via the dosing ratchet. In this way, the use of a more complicated connection to the dose setting member can be avoided.

In an embodiment of the invention, the dose delivery device further comprises a dose setting ratchet acting perpendicularly to a longitudinal axis of the device, and setting a dose by rotating the dose setting member involves no motion of any part of the device along said longitudinal axis of the device relatively to the dose setting member. In this way, a spring acting axially on the dose setting ratchet can be avoided, as it is easier to integrate the spring mechanism in the dose setting ratchet.

In an embodiment of the invention, a piece of the thread path on at least one thread connection is substituted by a combination of a straight path along a longitudinal axis of the device and a rotational path, and the end of the rotational path forms the stop of the dose injection. In this way an audible and tacticle feed back at the end of the injection is provided.

The invention can be obtained by a dose delivery device comprising a dose setting system and an injection system. The dose setting system is of a kind, where a scale drum is engaged with the housing via a thread and rotationally coupled to a dose setting member when a dose is set, and rotationally decoupled when a set dose is injected. A dose is set by rotating the dose setting member carrying the scale drum along. The dose setting member is locked against rotation during injection and the scale drum is returned to a zero position by pushing the scale drum longitudinally causing it to rotate due to the thread engagement with the housing.

Alternatively, the rotationally coupling between the scale drum and the dose setting member is a kind of ratchet which can be unidirectional or bidirectional. As the torque between the scale drum and the dose setting member due to the ratchet and to friction is higher than the torque between the dose setting member and the driver due to a dose setting ratchet between these two elements and friction, the dose setting member will carry the scale drum along. During injection the dose setting member is locked against rotation, and the scale drum is forced to rotate in its thread, which will cause the ratchet between the dose setting member and the scale drum to click.

In another embodiment a dose is set by rotating the scale drum, which then will carry the dose setting member along.

The injection system comprises a piston rod cooperating with a piston in a cartridge and locked against rotation relative to the housing. The piston rod is engaged with a dosing nut via a thread having a smaller pitch than the thread between the scale drum and the housing. The ratio between the two pitches is the gearing ratio. The dosing nut is rotational connected to the dose setting member via a gearing mechanism further described below. To set a dose, the dose setting member is rotated causing the dosing nut to rise along the piston rod, but less than the dose setting member. When injecting, the dose setting member and the dosing nut is rotational locked against rotation, and the force applied to the dose setting member is transferred to the dosing nut via the gearing mechanism. As also the piston rod is locked against rotation, the piston rod will advance as well causing the piston to expel medicine.

The gearing mechanism comprises a dual-threaded nut, which is longitudinally connected to the dosing nut. The two threads on the dual-threaded nut are headed in opposite directions, i.e. one is a normal right-handed thread and the other is a left-handed thread. The right-handed thread (or the left-handed thread) is connected with the housing, and the other thread is connected to a driver rotationally locked to the housing. When a dose is set, the dosing nut will force the dual-threaded nut to elevate along with the dosing nut causing it to rotate due to the thread engagement with the housing. This will cause the driver to elevate even further as it is affected both via the elevation of the dual-threaded nut and the relative rotation to the dual-threaded nut, which will also cause it to elevate as the thread is handed oppositely compared to the thread between the dual-threaded nut and the housing.

This means, that when the housing and the driver are moved relative to each other, the nut will rotate and move longitudinally a distance less than the driver. When injecting, the applied force on the dose setting member is transferred directly through the driver to the dual-threaded nut and further on to the dosing nut and the piston rod.

The pitches can be set to any value as long as the threads are not self-locking. This means that the loss of dosing force due to friction can be very low.

When setting a dose, a clicking sound is produced as a click item with saw teeth and rotationally coupled to the dose setting member is axially biased against corresponding saw teeth on the driver. When the dose setting member is rotated, the click item will jump up and down due to the saw teeth, indexing the dose setting member on certain positions around the axis and producing a clicking sound.

Alternatively, the dose setting click and indexing of the dose setting member can be radial between a click item locked to the driver and the dose setting member. This has the advantage, that the indexing torque can be set to be high and the spring force to engage the dose setting member and the scale drum can be set to be low, or to be zero if there is no engagement/disengagement.

It should be noted, that the dose delivery device can be designed to be either disposable or rechargeable and to contain one, two or multiple cartridges at the time. If the dose delivery device is designed to be rechargeable, the piston rod must be able to rotate when the cartridge holder is disconnected.

BRIEF DESCRIPTION OF THE FIGURES

In the following the invention is described in further details with reference to the drawings, wherein.

DETAILED DESCRIPTION

Figure 1:
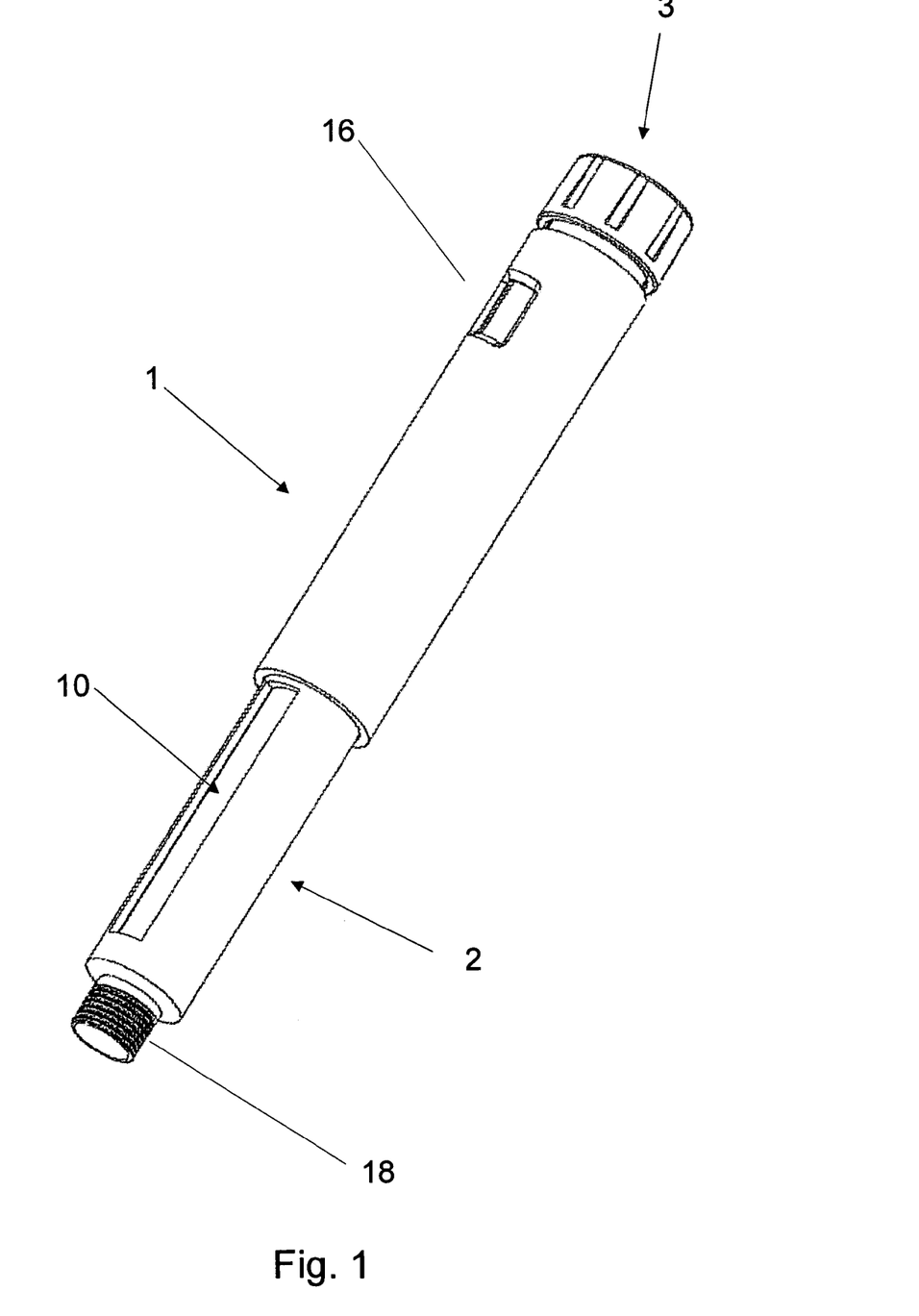
FIG. 1 shows a perspective view of a device according to the invention.

FIG. 1 shows a device according to the invention in an oblique view. Visible is the housing 1 comprising a window 16, where the amount of a set dose can be displayed, the dose setting member 3 by which a dose is set and injected and the cartridge holder 2 comprising a thread 18 for the attachment of a double-ended needle. The cartridge holder 2 also contains the medicine-filled cartridge 10. The cartridge 10 comprises a piston (not shown), which cooperates with the piston rod 7 of the injection system to expel a set dose of medicine from the cartridge 10 out through the needle. The cooperation between the different elements of the device will be described in the following.

The dose setting member 3 of the shown embodiment is to be comprehended as an element by which a dose can be both set and injected. In other embodiments of the invention, the functions of the dose setting member 3 are divided into two elements—a dose setting button and an injection button. In some embodiments, the dose setting function is part of the numbered scale drum 4.

The device comprises four frame parts which are locked relative to each other, i.e. the housing 1, the threaded tower 12, the rotational lock 31 and the cartridge holder 2. These parts are to be seen as one part, but can be produced in segments which are appropriate in relation to the assembling process.

Figure 2:
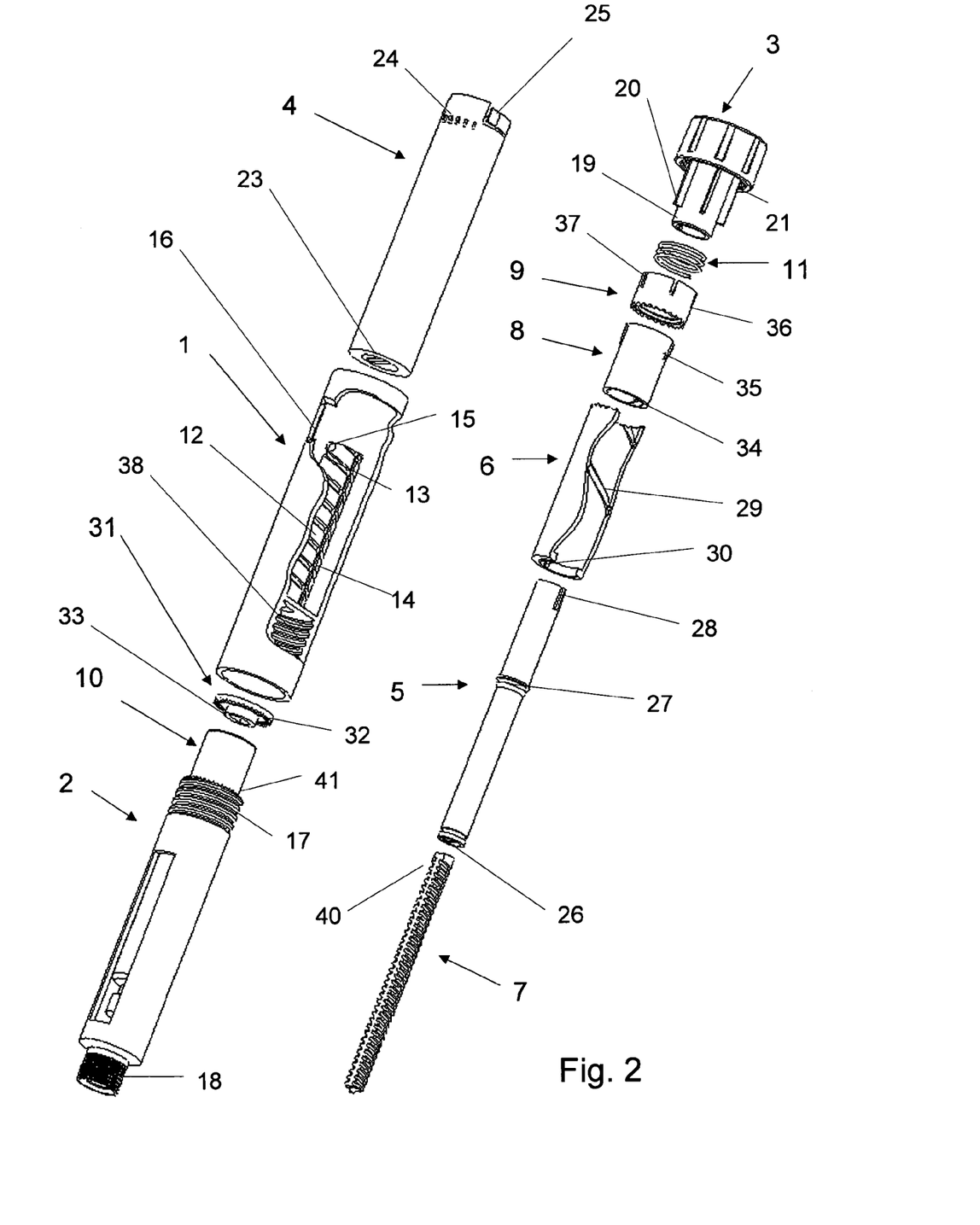
FIG. 2 shows an exploded view of a device according to the invention, FIG. 3 schematically shows a vertical sectional view of a device according to the invention ready to set a dose, FIG. 4 schematically shows a vertical sectional view of a device according to the invention where a dose has been set, FIG. 5 schematically shows a vertical sectional view of a device according to the invention where the dose setting member has been pushed and the scale drum is disengaged, FIG. 6 schematically shows a vertical sectional view of a device according to the invention where a dose has been injected but the dose setting member is still depressed.

In the shown embodiment the threaded tower 12 is an integrated part of the housing 1, as shown on FIG. 2. The rotational lock 31 is an independent part which is locked between the housing 1 and the cartridge holder 2, when the cartridge holder 2 containing a medicine-filled cartridge is mounted in the housing. The cartridge holder 2 is fixed to the housing 1 by a thread connection 17/38. Two sets of teeth 32/41 on the rotational lock 31 and on the cartridge holder 2 equally spaced around the centre axis of the device ensure, that the rotational lock is sufficient secured.

It should also be noted that the thread 13 engaging the scale drum 4, the thread knobs 15 engaging the dual-threaded nut 8 and the grooves 14 engaging the keys 30 of the driver 6 could be placed on the inner cylindrical surface of the housing 1, either all of them or some of them. This could remove the need for a threaded tower 12.

As shown in FIG. 1, a dosing nut 5 is engaged with a piston rod 7 via a thread. The piston rod 7 is locked against rotation relative to the housing via a key 32, which is part of the rotational lock 31, which is again part of the housing assembly. A dose setting member 3 is rotational locked to the dosing nut 5 via a key/groove connection 28/19. The dose setting member 3 is rotationally connected with a click item 9, which is engaged with the driver 6 via saw teeth 36/42 on both parts. A spring 11 is situated between the driver 6 and the click item 9, so that when the dose setting member 3 and the click item 9 are rotated, the click item 9 will jump up and down due to the saw teeth 34/42, which will provide a number of increments per round corresponding to specific amounts of medicine.

A gearing mechanism is situated between the dosing nut 5 and the dose setting member 3 in a manner, so that when the dose setting member 3 is being rotated to set a dose, the dosing nut 5 will elevate due to thread engagement, but the dose setting member will be elevated e.g. the double distance due to the gearing mechanism. The gearing mechanism is provided to make it easier to inject a preset dose, to make it more visible to the user that the dose setting member is being moved during an injection and to provide more space for numbers to be written on a scale drum 4. This will be further explained later.

The gearing mechanism comprises a dual-threaded nut 8 (see FIG. 2), which is longitudinally connected to the dosing nut via the flange 39 on the dual-threaded nut 8 and the flange 27 on the dosing nut 5. This can be seen in FIGS. 3-6. There are two threads on the dual-threaded nut, an outer 35 and an inner 34, which are headed in opposite directions, i.e. one is a normal right-handed thread and the other is a left-handed thread. The outer right-handed thread 35 is connected to the housing 1 and the inner left handed thread 34 is connected to a driver 6, which is rotationally locked to the threaded tower 12 in the housing 1 via key/groove 30/14 and preferable longitudinally guided by the scale drum 4 in order to avoid that medicine can be expelled, when a dose is set. When a dose is set, the dosing nut 5 will force the dual-threaded nut 8 to elevate along with the dosing nut 5 causing it to rotate due to the thread engagement 34/13 with the housing 1. As shown in FIG. 4, this will cause the driver 6 to elevate more than the dual-threaded nut 8 as it is affected in two ways: It is longitudinally elevated by the dual-threaded nut 8 and it is rotated in the thread engagement 35/29 between the two elements. As the thread is handed oppositely compared to the thread connection 34/13 between the dual-threaded nut 8 and the threaded tower 12, this will cause it to elevate further.

This means that when the housing 1 and the driver 6, which are relative rotationally locked via the key/groove 30/14, are moved longitudinally relative to each other, the dual-threaded nut will rotate and move longitudinally a distance smaller than the longitudinally distance moved by the driver. When injecting, the applied force on the dose setting member 3 is transferred to the dosing nut 5 via the driver 6 and the dual-threaded nut 8. A gearing in distance is achieved as the driver 6 moves a longer distance than the dosing nut 5 and the piston rod 7, and a gearing in force is achieved, as the loss of force due to friction is very low.

The pitches on the threads 34/35 on the dual-threaded nut 8 can be set to any value as long as the threads are not self-locking and they can thereby be set to be very high. This is very advantageous as it means that the loss of dosing force due to friction can be very low.

The gearing ratio obtained by the gearing mechanism are calculated as the sum of the pitch of the two threads 34/35 on the dual-threaded nut 8 divided by the pitch of the thread 34 engaging the thread 13 on the threaded tower. An example: The pitch on the thread 34 engaging the threaded tower 12 is 12 and the pitch of the thread 35 engaging the driver 6 is 18. The gearing ratio is (12+18)/12=2.5. In this case, the driver 6 and thereby the dose setting member 3 will move 25 mm when the dual-threaded nut 8 moves 10 mm.

The directions of the two threads 34/35 can be interchanged, so that the right-handed thread is left-handed and vice versa. The important matter is that they are headed in opposite directions.

To be able to display the amount of a set dose, a numbered scale drum 4 is part of the device. This can most clearly be seen on FIG. 2. The scale drum 4 engages with the threaded tower 12 via a thread connection 23/13. The scale drum 4 comprises a number of teeth 24 on the outer cylinder equally spaced around the centre axis of the device. The angle between them corresponds to the angle between two units of the medicine or a division thereof. As shown on FIG. 2, some of them have been cut away, to simplify the production of the scale drum 4. The teeth 24 are engaging a set of teeth 21 of the inner cylinder of the dose setting member 3 as shown on FIGS. 3-6. The engagement is ensured by a spring 11. When a dose is set, the scale drum 4 is rotated along with the dose setting member 3. As the pitch on the scale drum 4 corresponds to the gearing ratio of the gearing mechanism, the scale drum 4 and the dose setting member 3 elevates the same distance. When a set dose is injected, the dose setting member 3 is pushed down a distance, which will disengage the rotational connection between the parts. The scale drum 4 will hereafter be pressed down by the driver 6 and forced to rotate in the thread connection 23/13 with the threaded tower 12, until it abuts a rotational stop. This stop will preferable be the "end of dose" stop as well.

Two ratchet arms 25 are provided on the scale drum 4. During injection these ratchet arms 25 will produce a clicking sound in a set of teeth 22 provided in the inner and upper cylindrical part of the dose setting member 3. These ratchet arms 25 are unidirectional and ensures at the same time, that the scale drum 4 will not be able to rotate backwards, which could retract the piston rod 7 in the housing 1.

The pitch of the thread 23 on the scale drum 4 must correspond to the pitch of piston rod 7 multiplied with the gearing ratio of the gearing mechanism. An example: If the pitch on the piston rod 7 is 3.6 and the gearing ratio is 2.5, then the pitch on the scale drum 4 must be 3.6×2.5=9.

Figure 3:
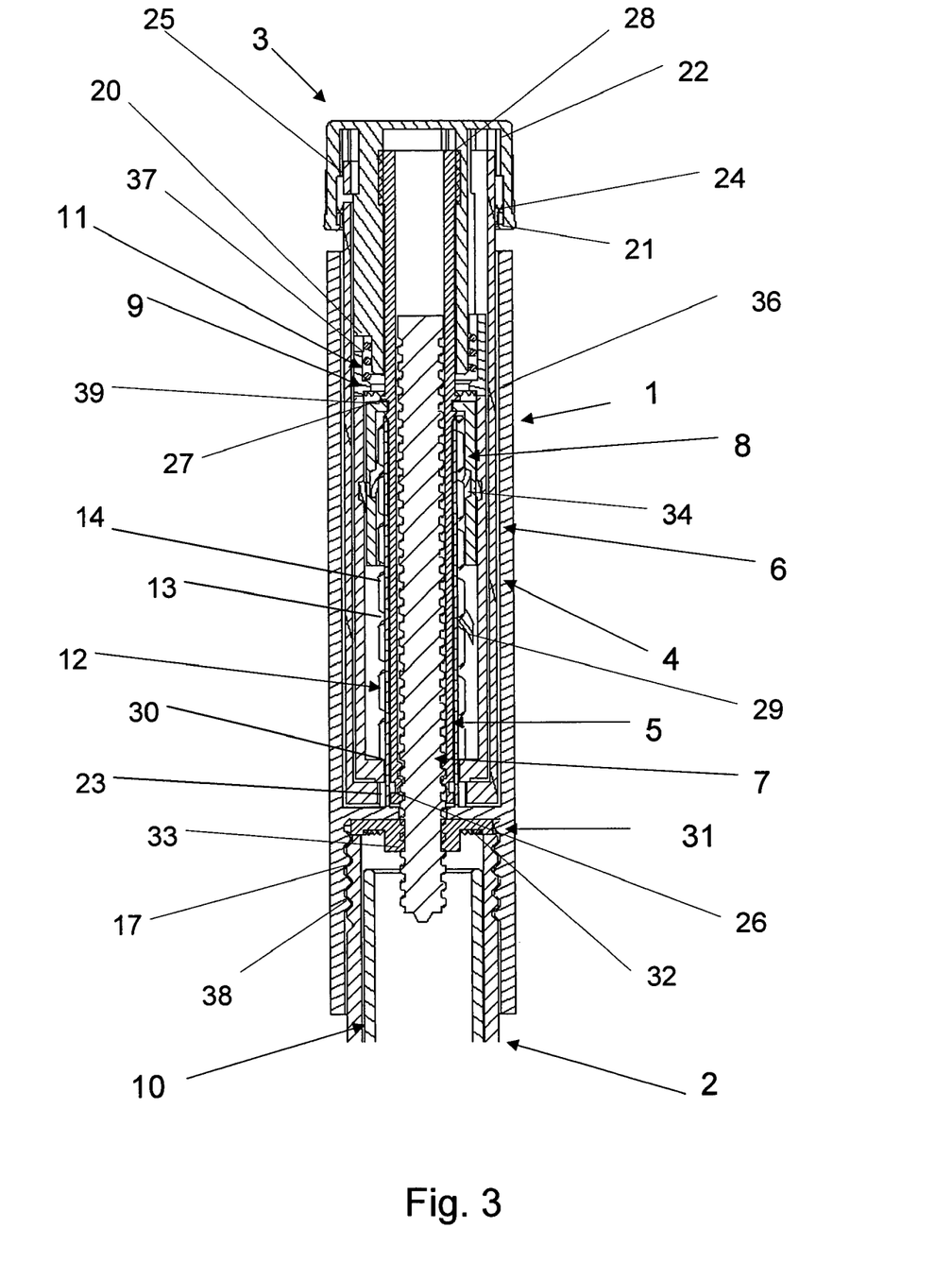
Figure 4:
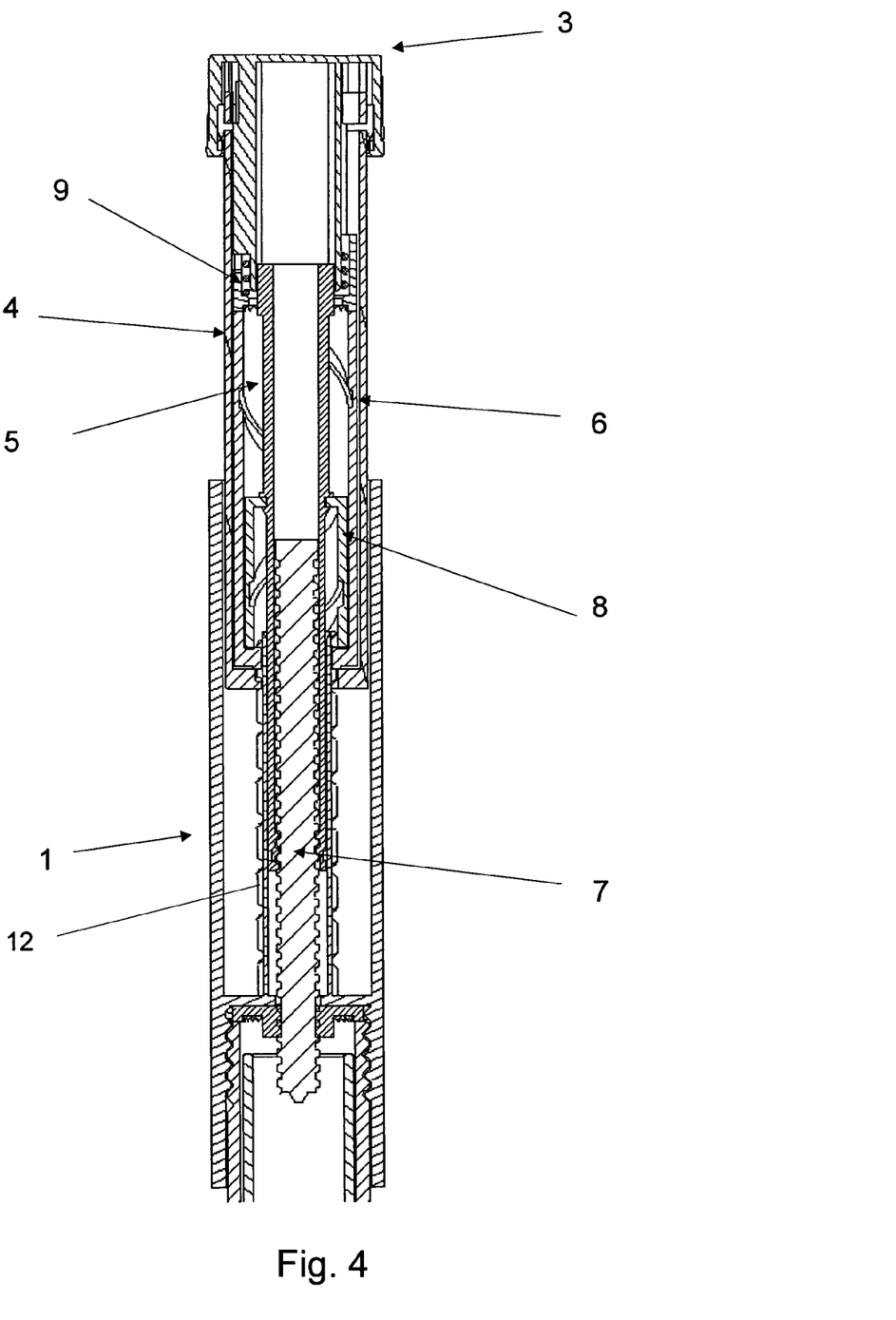

To prevent that a higher dose is set, than there are medicine left in the cartridge, a rotational stop 40 is provided in the end of the piston rod 7 pointing away from the needle end, which can be seen on FIG. 3. When the dosing nut reaches the rotational stop, the dosing nut 5 and thereby the dose setting member 3 can no longer be rotated.

In the following all sequences related to having an injection are described with references to FIGS. 3-6.

FIG. 3 shows a device ready for setting a dose. To set a dose, the dose setting member 3 is rotated clockwise, which will cause the device to produce a clicking sound for each increment due to the saw teeth interface 36/42 between the click item 9 and the driver 6, each click corresponding to a unit of the contained medicine. Furthermore, this interface will provide a number of preferred positions of the dose setting member to ensure the precision of the device. The dose setting member 3 rotates the dosing nut 5 as well, and this will now elevate from a zero position. The dose setting member 3 will elevate as well, but due to the gearing mechanism, it will elevate more than the dosing nut. The scale drum 4 is rotated along with the dose setting member 3 due to the teeth engagement 21/24 and will elevate a distance corresponding to the elevation of the dose setting member 3 due to the thread engagement 23/13 with the threaded tower 12.

In FIG. 4, a dose has been set. It is now clearly seen that the dose setting member 3, the driver 6 and the scale drum 4 has elevated one distance, and that the dual-threaded nut 8 and the dosing nut 5 has elevated a shorter distance.

Figure 5:
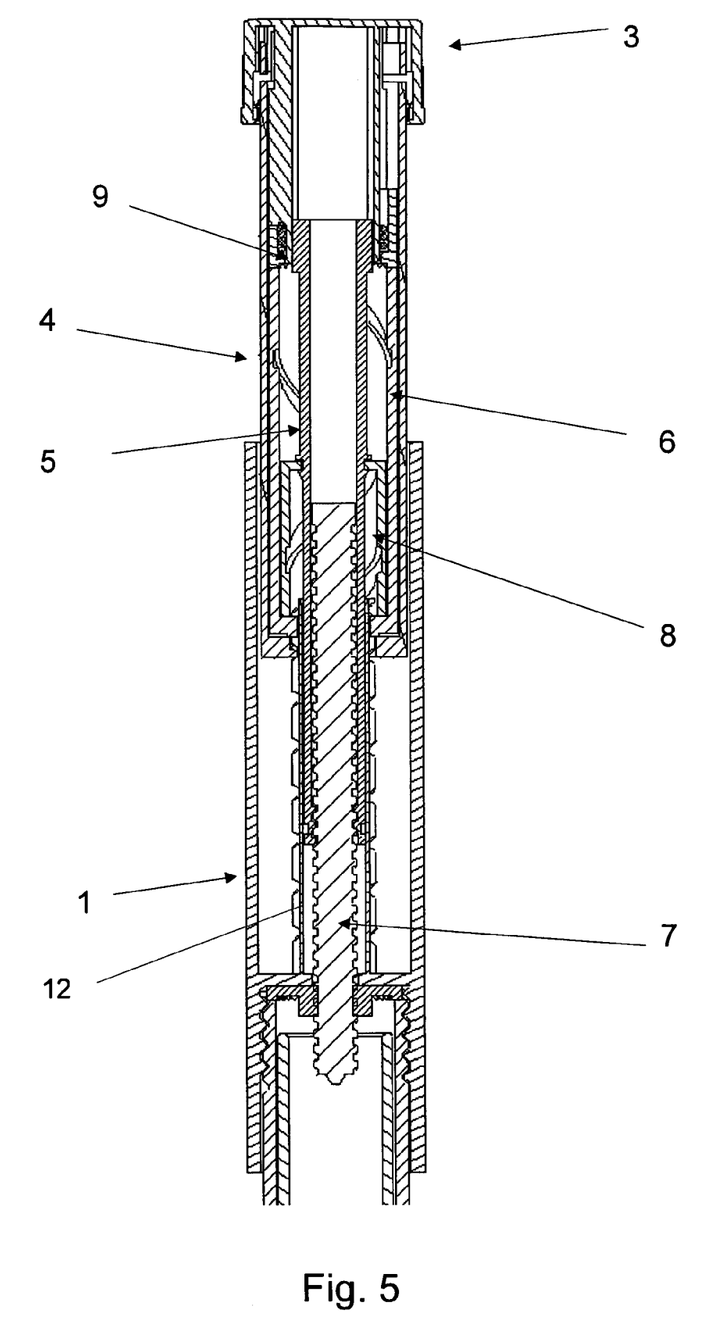

In FIG. 5 the dose setting member has been pushed down, and further depression of the dose setting member 3 will cause the driver to move and medicine to be expelled. This causes the dose setting member to be rotationally locked to the driver 6 as the click item 9 and the driver 6 are pressed together. Additionally, the dose setting member 3 and the scale drum 4 are disengaged.

Figure 6:
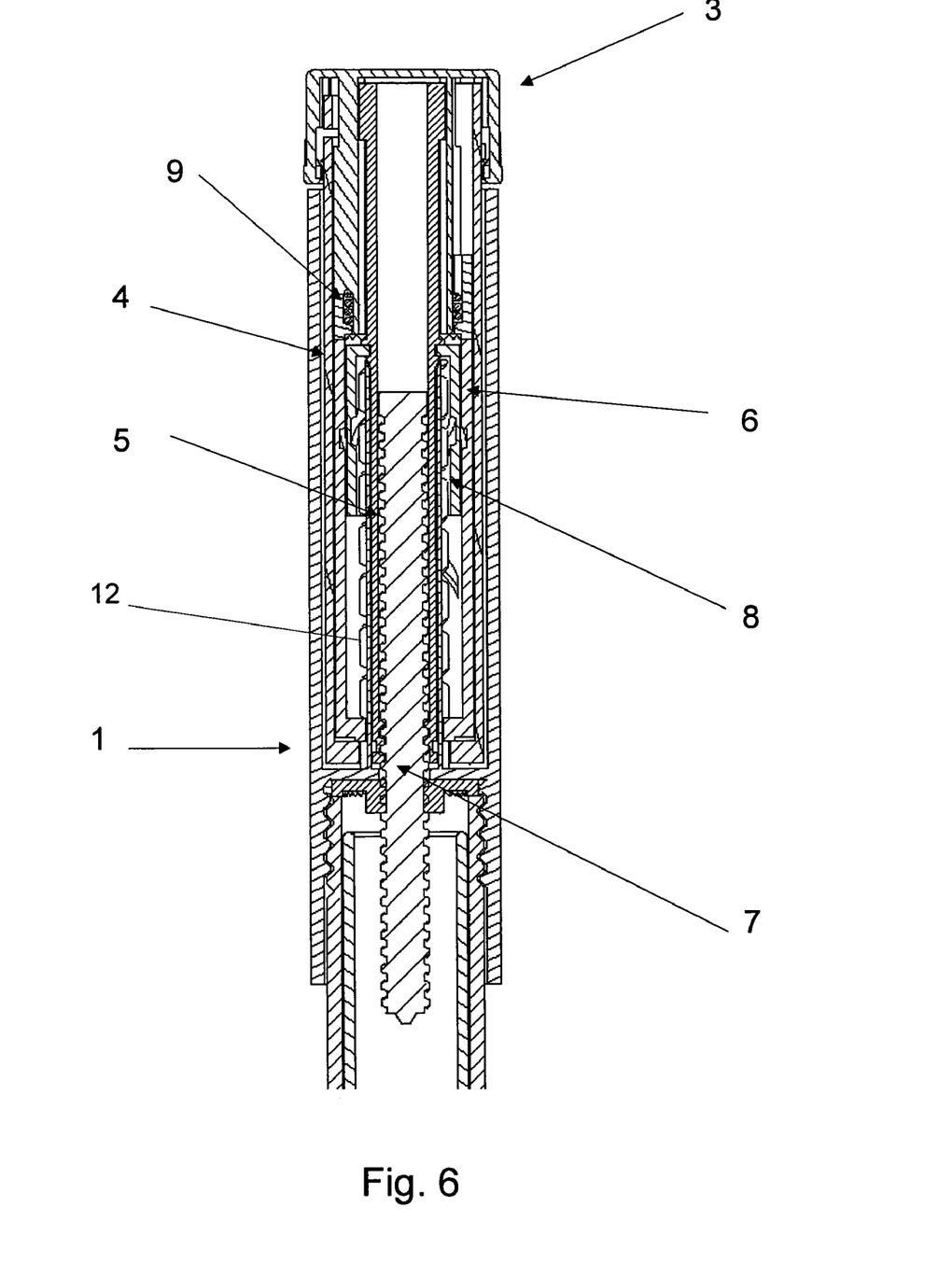

FIG. 6 shows a device, where the injection has just been accomplished and the dose setting member 3 is still depressed. The scale drum 4 has been pushed back to its zero position by the driver 6. The dosing nut 5 has also been pushed back to its zero position moving a shorter distance due to the gearing mechanism. As the dose setting member 3 and the dosing nut 5 are interconnected via key/groove 28/19, neither of them has been rotating during injection. As also the piston rod is prevented from rotating due to the key/groove connection between the rotational lock 31 and the piston rod 7, the piston rod 7 has been carried along with the dosing nut 5 moving the same distance. Comparing FIG. 3 and FIG. 6 it is clear that the piston rod has moved. As the piston rod 7 cooperates with the piston of the cartridge 10, the piston has been moved the same distance as well, which has caused medicine to be expelled through the double-ended needle on the cartridge holder 2.

Figure 7:
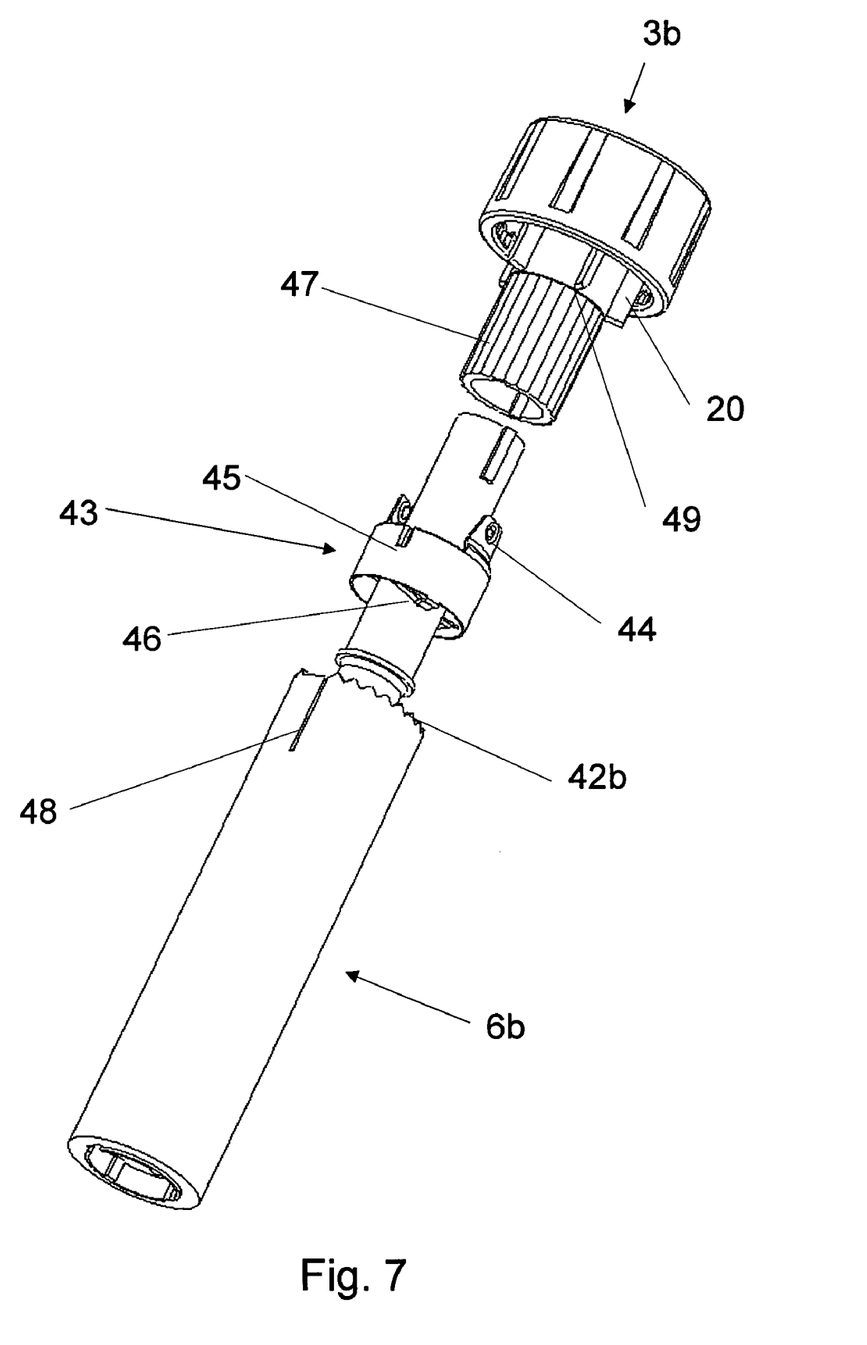
FIG. 7 shows an exploded view of an embodiment of a device according to the invention with radial dose setting click, FIG. 8 schematically shows a vertical sectional view of an embodiment of a device according to the invention with radial dose setting click.
Figure 8:
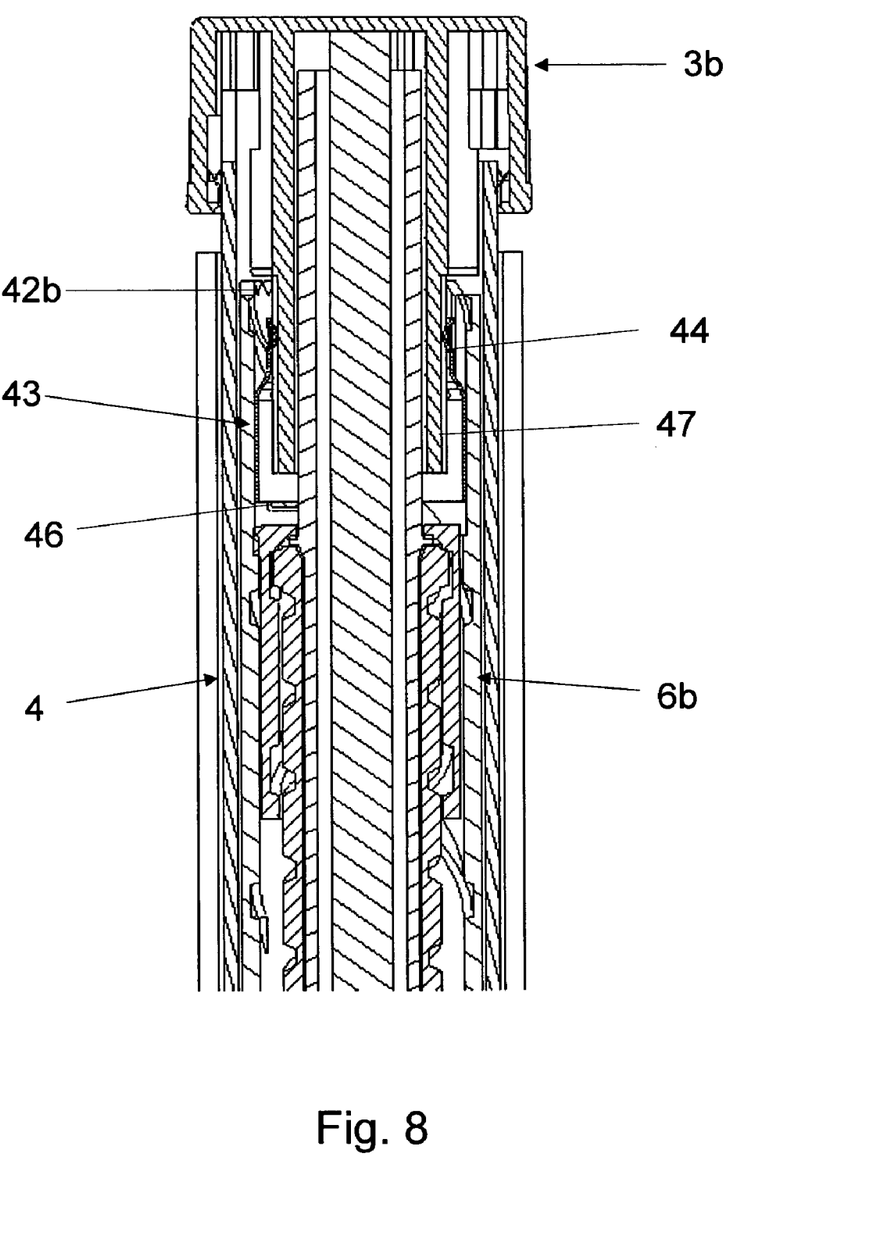

FIGS. 7 and 8 show an embodiment with a radial dose setting click. A cylindrical click item 43 preferable made in sheet metal is mounted in the driver 6b and is locked against rotation via a key/groove connection 45/48 and as it mates a recess in the driver 6b, it is also locked against axial displacement. Two protrusions 44 with inward pointing depressions are integrated with the click item 43 and pointing away from the needle end. These depressions fit firmly into grooves 47 equally spaced around the axis of the dose setting member 3b. As the click item 43 is locked against rotation due to the connection with the driver 6b, a rotation of the dose setting member 3b will index the dose setting member 3b in intervals corresponding to the number of grooves 47, at the same time producing a clicking sound and a tactile feed-back when rotating the dose setting member 3b. To create some distance between the saw teeth 42b on the driver 6b and the saw teeth 49 on the dose setting member 3b, two spring arms 46 are integrated in click item 43. The length of the movement of the axial spring is very limited, so that when the push-button is not depressed, the spring force is zero, and the dose setting member 3b and the scale drum are not affected by the spring. When a dose is to be injected, the dose setting member 3b is pushed and the saw teeth connection 42b/49 will prevent the dose setting member 3b from rotating.

Figure 9:
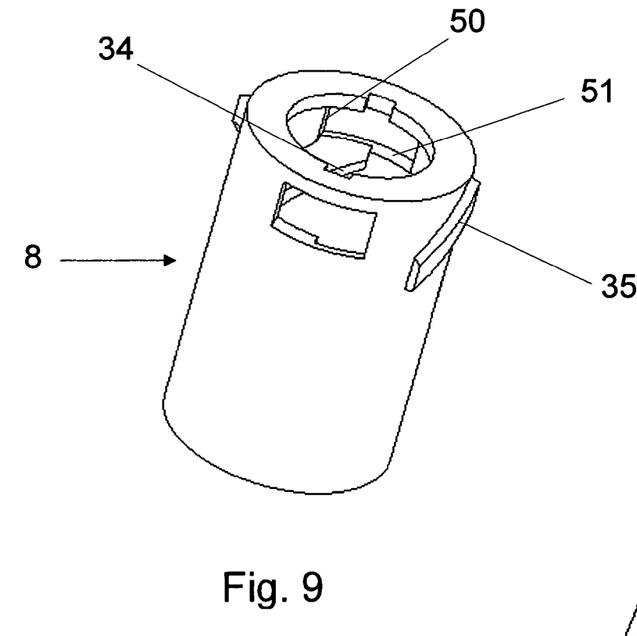
FIGS. 9-12 show another embodiment of a device according to the invention, which produces a tactile and audible click at the end of the injection.
Figure 10:
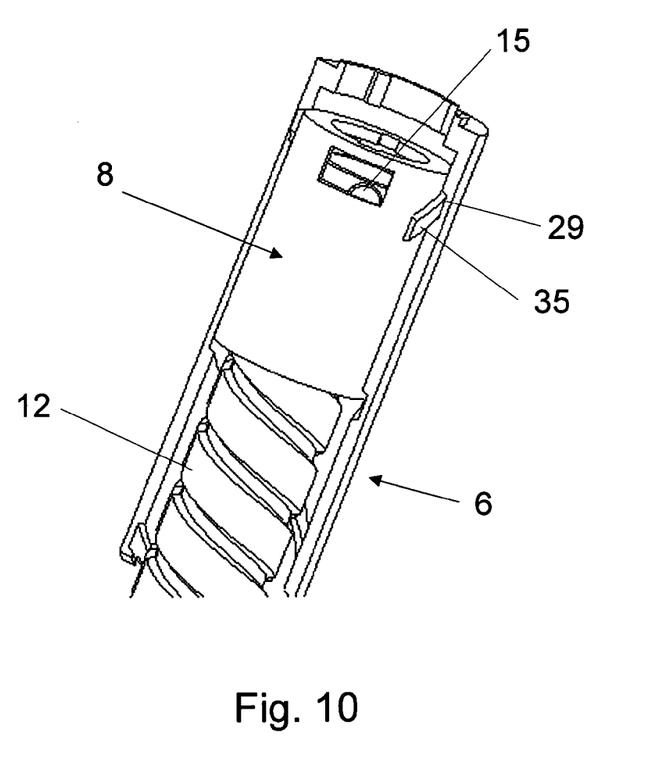
Figures 11, 12:
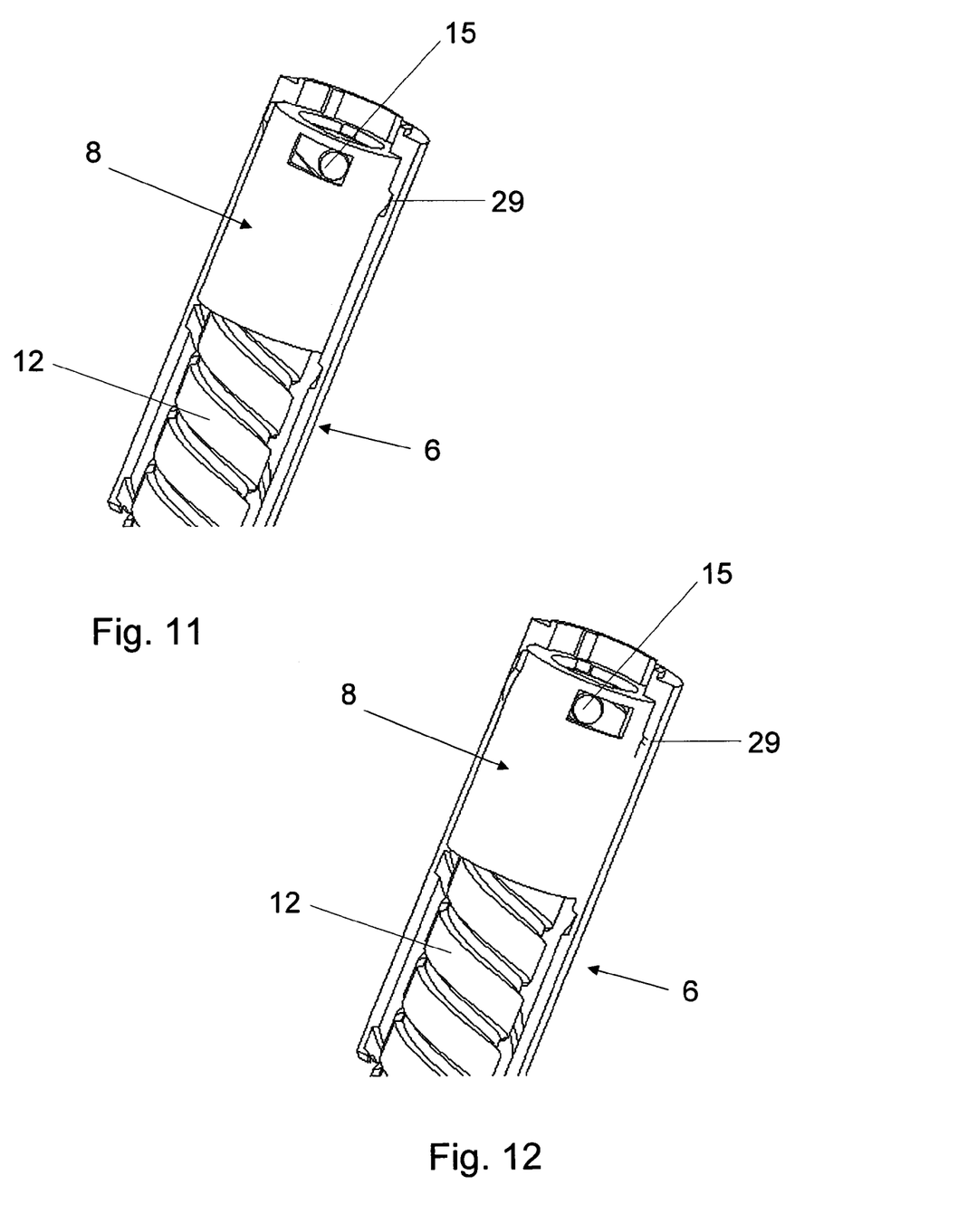

FIGS. 9 to 12 show an embodiment which produces a tactile and audible click at the end of the injection in order to make it clear for the user, that the set dose has been fully and successfully injected. As can be seen in FIG. 9 the inner thread 34 of the dual-threaded nut 8 is changed in such a way, that the thread stops before the end of the injection, and thereafter is followed by a straight path 50 parallel to the axis of the device, which extrudes to the end of the dual-threaded nut 8. This path is followed by a rotational path 51, which ends where the inner thread 34 would normally end. These two paths have the influence on the injection, that the straight path 50 will disable the gearing a distance e.g. corresponding to two units, and the rotational path 51 will allow the driver 6 and the dose setting member 3 to be depressed without moving the dual-threaded nut 8 axially, as it will only rotate. If the axial path 50 starts when two units are remaining, the last two units will be expelled starting when two units are remaining and ending when one unit is remaining, and therefore the last unit is "empty" and the device is unloaded when the dose setting member is depressed what corresponds to the last unit. This will speed up the dose setting nut in end of the injection with a tactile and audible signal as consequence. In FIGS. 10-12, the relative positions of the dual-threaded nut 8 and the thread knob 15 of the threaded tower 12 can be seen when entering the straight and rotational paths 50/51.

The invention claimed is:

1. A dose delivery device with a gearing mechanism comprising
    a housing comprising a first thread,
    a driver comprising a second thread,
    a dual threaded nut including first nut thread engaged with the first thread of the housing and second nut thread engaged with the second thread of the driver, respectively,
    a dosing nut comprising a third thread,
    a dose setting member,
    a push button and
    a piston rod comprising a fourth thread engaged with the third thread of the dosing nut and being rotationally locked to the housing during dose setting and injection,
    wherein the housing and the driver are relatively connected via a key and a groove allowing axial movement of the driver relative to the housing during dose setting and injection without allowing rotational movement of the driver relative to the housing during dose setting and injection,
    wherein axial movement of the driver during dose setting and injection causes the dual threaded nut to rotate and to move axially, only a shorter distance than the driver,
    wherein the dual threaded nut is connected with the dosing nut in a way that allows relative rotational movement but not relative axial movement between the dual threaded nut and the dosing nut,
    wherein a dose can be set by rotating the dose setting member, whereby the push button is elevated from one end of the device a distance proportional to the set dose from a position fixed relative to the housing,
    wherein the set dose can then be injected by pressing the push button back to its non-elevated position, through which motion of the push button the piston rod will move the same or a different distance due to the gearing, and
    wherein one of the first nut thread and second nut thread is left-handed and the other is right-handed.

2. A dose delivery device according to claim 1, wherein a piece of a thread path on the dual threaded nut, which engages the first thread of the housing, is substituted by a combination of a straight path parallel to a longitudinal axis of the device, and a rotational path around a center axis of the device, and wherein the end of the rotational path forms the stop of the dose injection.

3. A dose delivery device with a gearing mechanism according to claim 1 further comprising a scale drum, which rotates together with the dose setting member when a dose is set, and which rotates relative to the dose setting member when the dose is being injected.

4. A dose delivery device with a gearing mechanism according to claim 3, wherein the scale drum and the dose setting member are coupled together during dose setting and de-coupled during injection.

* * * * *